(12) United States Patent
Krywyj

(10) Patent No.: US 9,234,812 B2
(45) Date of Patent: Jan. 12, 2016

(54) WATER MAINS INSPECTION AND SERVICING

(75) Inventor: Daniel Krywyj, Derby (GB)

(73) Assignee: JD7 LIMITED, Derby, Derbyshire (GB)

( * ) Notice: Subject to any disclaimer, the term of this patent is extended or adjusted under 35 U.S.C. 154(b) by 1088 days.

(21) Appl. No.: 13/254,442

(22) PCT Filed: Mar. 1, 2010

(86) PCT No.: PCT/GB2010/050356
§ 371 (c)(1),
(2), (4) Date: Dec. 15, 2011

(87) PCT Pub. No.: WO2010/100480
PCT Pub. Date: Sep. 10, 2010

(65) Prior Publication Data
US 2012/0098955 A1 Apr. 26, 2012

(30) Foreign Application Priority Data
Mar. 3, 2009 (GB) .................................. 0903589.0

(51) Int. Cl.
*H04N 7/18* (2006.01)
*G01M 3/00* (2006.01)
*G01N 21/954* (2006.01)
*G01N 29/06* (2006.01)
*G01N 29/265* (2006.01)
*E21B 7/14* (2006.01)

(52) U.S. Cl.
CPC .............. *G01M 3/005* (2013.01); *G01N 21/954* (2013.01); *G01N 29/0654* (2013.01); *G01N 29/265* (2013.01); *G01N 2021/9544* (2013.01); *G01N 2291/2636* (2013.01)

(58) Field of Classification Search
CPC ...... G01M 3/005; G01M 3/38; G01N 21/954; E03F 7/12; H04N 7/183; E21B 47/122; E21B 45/00; E21B 47/14; E21B 10/42; E21B 34/12; E21B 34/16; E21B 3/00; E21B 47/06; E21B 7/00; E21B 2034/005; E21B 21/002; E21B 23/06; E21B 29/002; E21B 33/127; E21B 34/066
USPC ........................................................... 348/84
See application file for complete search history.

(56) References Cited

U.S. PATENT DOCUMENTS

| 3,186,481 | A | | 6/1965 | Foster |
| 3,409,897 | A | * | 11/1968 | Bosselaar et al. ............ 346/33 S |
| 3,413,653 | A | * | 11/1968 | Wood ............................ 346/33 S |
| 3,478,576 | A | * | 11/1969 | Bogle .......................... 73/40.5 A |
| 3,575,040 | A | * | 4/1971 | Bosselaar .................... 73/40.5 A |

(Continued)

FOREIGN PATENT DOCUMENTS

| DE | 3840994 | 6/1990 |
| DE | 4105446 | 8/1991 |

(Continued)

*Primary Examiner* — Sath V Perungavoor
*Assistant Examiner* — Howard D Brown, Jr.
(74) *Attorney, Agent, or Firm* — Blakely Sokoloff Taylor & Zafman LLP

(57) ABSTRACT

An inspection system for internal pipe inspection, comprises a feed cable (30), and a camera in the inspection head (32) at a remote end of the feed cable. Optional additional components include an ultrasound system (40), a steering arrangement with the guide roller (35) for the camera, a product release system (repair head 60), and a magnetic drive system.

10 Claims, 4 Drawing Sheets

(56) References Cited

U.S. PATENT DOCUMENTS

| | | | |
|---|---|---|---|
| 4,172,379 A * | 10/1979 | Van Tilburg et al. | 73/40.5 A |
| 4,382,290 A | 5/1983 | Havira | |
| 4,525,815 A | 6/1985 | Watson | |
| 4,732,156 A | 3/1988 | Nakamura | |
| 4,845,990 A | 7/1989 | Kitzinger et al. | |
| 4,974,168 A * | 11/1990 | Marx | H04N 7/185 348/125 |
| 4,998,282 A | 3/1991 | Shishido et al. | |
| 5,025,670 A * | 6/1991 | McNulty | F16L 41/06 73/865.8 |
| 5,084,764 A * | 1/1992 | Day | 348/84 |
| 5,285,689 A * | 2/1994 | Hapstack | G01N 29/265 324/220 |
| 5,313,950 A * | 5/1994 | Ishikawa | A61B 8/12 600/459 |
| 5,543,972 A * | 8/1996 | Kamewada | E21B 47/0002 175/49 |
| 5,635,784 A * | 6/1997 | Seale | 310/90.5 |
| 5,808,239 A * | 9/1998 | Olsson | 174/113 C |
| 6,263,534 B1 | 7/2001 | McCann et al. | 15/3.5 |
| 6,820,653 B1 * | 11/2004 | Schempf et al. | 138/98 |
| 8,098,063 B2 * | 1/2012 | Paulson | F16L 55/38 324/220 |
| 2004/0083829 A1 * | 5/2004 | Chapman et al. | 73/865.8 |
| 2004/0183899 A1 * | 9/2004 | Shiota | 348/84 |
| 2006/0288756 A1 * | 12/2006 | De Meurechy | 73/1.01 |
| 2009/0028670 A1 * | 1/2009 | Garcia | B25J 18/06 414/7 |
| 2010/0200275 A1 * | 8/2010 | Kim | H02G 5/063 174/21 JS |
| 2012/0098955 A1 * | 4/2012 | Krywyj | G01M 3/005 348/84 |

FOREIGN PATENT DOCUMENTS

| | | | | |
|---|---|---|---|---|
| DE | 4204174 | 8/1993 | | |
| EP | 0078072 | 5/1983 | | |
| EP | 0 621 437 A1 | 10/1994 | | |
| EP | 0909783 | 4/1999 | | |
| FR | 002842883 | * 9/2004 | | F16L 55/28 |
| GB | 1243613 | 8/1971 | | |
| GB | 2275981 | 9/1994 | | |
| GB | 2328488 | 2/1999 | | |
| JP | 04/299217 | 10/1992 | | |
| JP | 10-26615 | 1/1998 | | |
| JP | 2000092472 | * 3/2000 | | H04N 7/18 |
| WO | WO 92/21965 | 12/1992 | | |

* cited by examiner

WATER MAINS INSPECTION AND SERVICING

This is a non-provisional application claiming the benefit of International Application No. PCT/GB2010/050356 filed Mar. 1, 2010.

FIELD OF THE INVENTION

This invention relates to the inspection and/or servicing of fluid carrying pipes, such as mains water systems.

BACKGROUND OF THE INVENTION

Within the water industry, there is an increasing demand for routine repair works and maintenance/inspection works to be carried out without disruption of the water network services. Thus, there is a desire to maintain operational pressures and flows. In addition, it is desirable to minimise the amount of excavation required to find the location of leaks in underground pipes.

It is known therefore to introduce a camera into a pipe for detecting leaks by means of visual internal inspection. However, many difficulties arise in the feeding of a camera over a long distance. Furthermore, visual inspection is not fully reliable in detecting leaks.

SUMMARY OF THE INVENTION

According to a first aspect of the invention, there is provided an inspection system for internal pipe inspection, comprising:
 a feed cable;
 an ultrasound probe and an ultrasound sensor along the feed cable;
 a processor for analysing the detected ultrasound signals; and
 a display for displaying the analysed signals.

This provides analysis of the pipe wall properties from inside the pipe, and can be used to internally map the integrity of the pipe by providing internal and external profiles. The ultrasound probe is preferably arranged to direct the probe signal in a direction parallel with the feed cable elongate axis, and the system further comprises a means for redirecting the signal to a radial pipe direction (for example a reflector or prism), wherein the reflector is rotationally driven to scan all radial directions. This provides a compact way to implement 360 degree imaging of the pipe using a single ultrasound beam.

The rotational drive can be implemented using a motor sealed in a chamber having an end wall, wherein the motor has an output disc adjacent the end wall and comprising a magnet arrangement. The reflector then comprises an input drive disc adjacent the outer surface of the end wall and which comprises a magnet arrangement corresponding to the output disc.

This provides a magnetic clutch which can operate across a fluid seal, so that the motor can remain in a watertight environment even though the output is driving a reflector which is in immersed in the liquid in the pipe.

According to another aspect of the invention, there is provided a camera inspection system for internal pipe inspection, comprising:
 a feed cable;
 camera at a remote end of the feed cable; and
 a guide roller mounted at the remote end of the feed cable having a rotation axis perpendicular to the length of the feed cable, and offset from an elongate axis of the feed cable,
 wherein the feed cable is rotatable about the elongate axis, thereby to change the angular position of the guide wheel within the pipe.

This system enables the camera to be steered as it is advanced in a pipe. The roller acts as a deflection tool so that the camera head can be guided around bends and T-pieces. The guide roller is preferably located within the field of view of the camera, so that visual camera feedback is provided both of the pipe ahead and the current position of the roller.

According to another aspect of the invention, there is provided a product delivery system for providing a product at a desired location internally of a pipe, comprising:
 a feed cable;
 a product chamber along the feed cable comprising a storage vessel and a release aperture;
 wherein the storage vessel is controllable between a first configuration in which the storage vessel contents are retained, and a second configuration in which the storage vessel contents can escape through the release aperture.

This arrangement enables the contents of a storage vessel to be released remotely into a desired location within a pipe. This can be a repair product or material which is for treating a localised defect in the pipe.

This can use a magnetic clutch and motor arrangement as explained above.

The inspection head can further comprise a hydrophone arrangement and a display system is then provided for displaying hydrophone frequencies, such that frequency ranges corresponding to leaks can be identified.

The feed cable can comprise reinforcing rods within an outer sheath, wherein the outer sheath is narrower in the region of the remote end to provide increased bending flexibility compared to the opposite end of the feed cable. This provides the desired flexibility of the head, but maintains the required strength and resistance to buckling required by the push/pull drive arrangement.

A drive arrangement is preferably provided for driving the feed cable, wherein the drive arrangement comprises:
 a coupling for connection to the pipe, and comprising a venting arrangement such that a first side of the venting arrangement is at the pressure of the pipe content and a second side of the venting arrangement is at a lower pressure;
 a motor and a roller arrangement within a housing, connected to the coupling, on the second side of the venting arrangement.

This provides a drive arrangement which is isolated from the pipe pressure, but the venting arrangement avoids the need for seals around the feed cable. The housing is preferably rotatable with respect to the coupling thereby to change the angular orientation of the feed cable. In this way, the linear cable position and angular orientation can be controlled in a reliable manner.

The venting arrangement can comprise a first bore on the first side leading to an internal chamber, a second bore on the second side also leading to the internal chamber and a vent valve which vents the internal chamber to the outside. The feed cable passes through the first and second bores, with clearance around the feed cable. This clearance means that seals are not needed, and the use of an internal chamber means that fluid flow loss is limited.

According to another aspect of the invention, there is provided a cable arrangement for feeding an inspection and/or maintenance system internally into a pipe, comprising reinforcing rods within an outer sheath, wherein the outer sheath is narrower in the region of a remote end to which an inspection and/or maintenance component is to be provided to provide increased bending flexibility, compared to the opposite end of the feed cable. This cable arrangement is of general interest for cables to be pushed remotely over long distances.

According to another aspect of the invention, there is provided a drive arrangement for driving an internal pipe servicing or inspection component, comprising:
- a motor sealed in a chamber having an end wall, wherein the motor has an output disc adjacent the end wall and comprising a magnet arrangement; and
- the internal pipe servicing or inspection component,
- wherein the internal pipe servicing or inspection component comprises an input drive disc adjacent the outer surface of the end wall and which comprises a magnet arrangement corresponding to the output disc.

This drive arrangement can be used to provide watertight coupling between a motor and a driven component within a pipe.

According to another aspect of the invention, there is provided a drive arrangement for driving a feed cable into a pipe, comprising:
- a coupling for connection to the pipe, and comprising a venting arrangement such that a first side of the venting arrangement is at the pressure of the pipe content and a second side of the venting arrangement is at a lower pressure;
- a motor and a roller arrangement within a housing, connected to the coupling, on the second side of the venting arrangement,
- wherein the venting arrangement comprises a first bore on the first side leading to an internal chamber, a second bore on the second side also leading to the internal chamber and a vent valve which vents the internal chamber to the outside, and wherein the feed cable passes through the first and second bores, with clearance around the feed cable.

This drive arrangement enables driving of a cable with live pressures in the pipe.

According to another aspect of the invention, there is provided a method of steering a camera within a pipe, in which the camera is mouted at a remote end of a feed cable, the method comprising
- using the camera image, viewing the location of a guide roller mounted at the remote end of the feed cable, which has a rotation axis perpendicular to the length of the feed cable, and offset from an elongate axis of the feed cable, and
- rotating the feed cable about the elongate axis thereby to control the angular position of the guide wheel within the pipe.

BRIEF DESCRIPTION OF THE DRAWINGS

Examples of the invention will now be described in detail with reference to the accompanying drawings, in which.

DETAILED DESCRIPTION

The invention relates to servicing and monitoring equipment for the interior of pipes.

Before describing the system of the invention, it will first be explained how the equipment can be launched into a pipe of a water mains system using a launch chamber, such that operational pressures and flows within the water system can be maintained.

Figure 1:
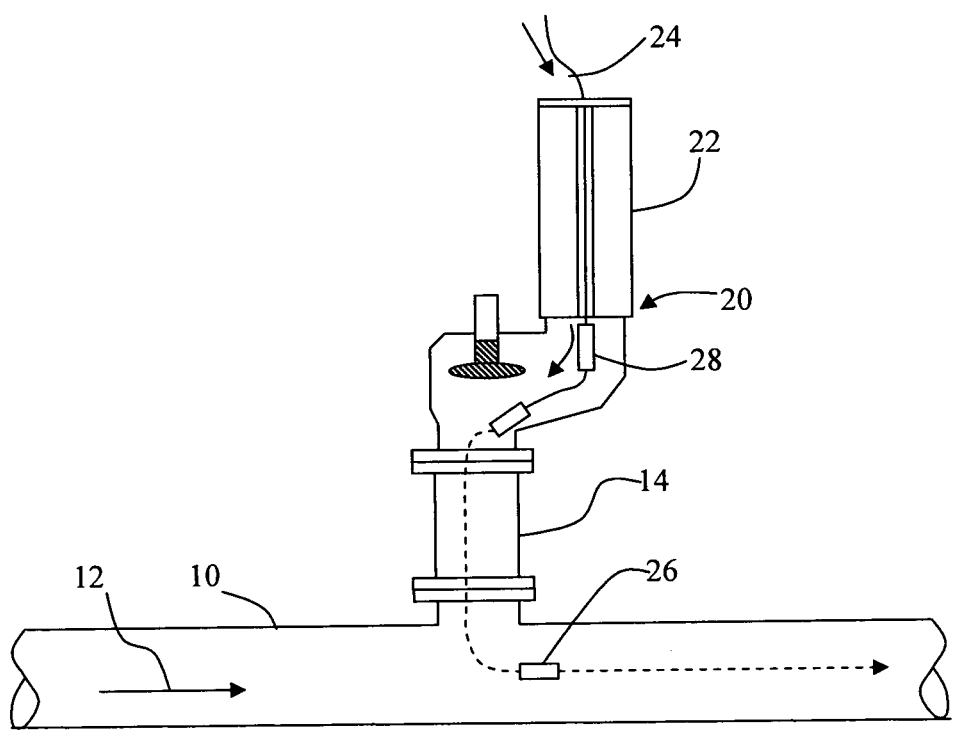
FIG. 1 shows how the inspection/repair system of the invention can be introduced into a pipe.

FIG. 1 shows the basic layout. A mains water pipe 10 carries a pressurised water flow 12. At a point along the pipe 10, there is an existing fire hydrant, which comprises a riser section 14 and a valve section 16. The valve section 16 has a control handle 18 which controls the flow of water from the mains pipe to an outlet 20 of the fire hydrant.

A launch chamber 22 can be provided in the form of a cover used for launching equipment into the mains water flow and which is coupled to the outlet 20.

FIG. 1 shows a control rod 24 passing through the chamber 22, and used to push a device 26 into the mains pipe 10 from an initial launch position shown as 28.

The invention relates specifically to the device 26, which is for leak detection and/or repair.

The device of the invention has a number of components, which can be used in combination or in isolation, depending on the intended work being carried out.

Figure 2:
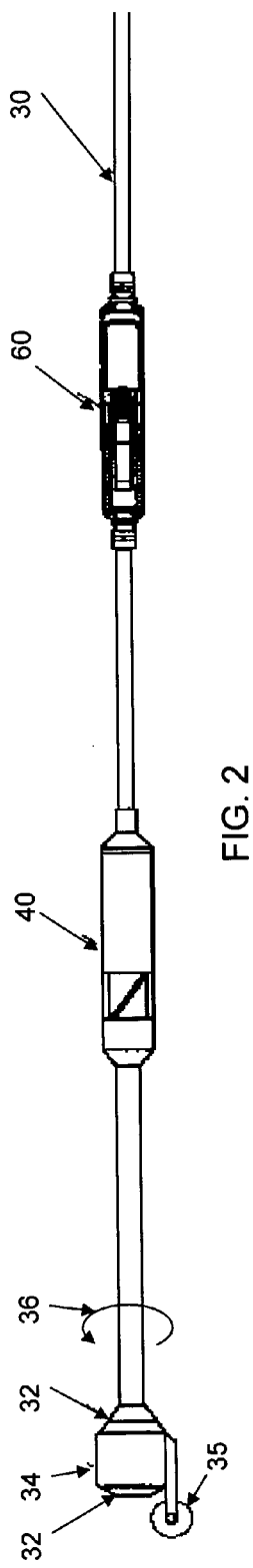
FIG. 2 shows an example of the inspection/repair system of the invention.

FIG. 2 shows all the components of the system of the invention in one connection.

The system comprises a feed cable 30, with an inspection head 32 at a remote end of the feed cable. The inspection head comprises a camera with a light ring for illuminating the path in front. It also includes a sonde (acoustic output probe) used to enable location of the head from above the ground, and a hydrophone for detecting sound within the interior of the pipe.

The head acts as a lead device at the remote end of the cable 30, and the other devices (described below) are positioned in series behind the inspection head.

The camera is used to relay real-time images, and the hydrophone is used to listen for frequency ranges identifying leaks within pipework when the head 32 passes such failures or defects.

The head 32 includes a guiding portion 34 which has a guide roller 35 (such as wheel, bearing or track) mounted at the remote end of the feed cable. The guide wheel has a rotation axis perpendicular to the length of the feed cable, i.e. it rolls as the feed cable moves along the pipe. The roller may comprises a series of rollers. However, the axis (or the axis of one of the rollers) is offset from the elongate feed cable axis, so that the head 32 rests on the wheel, with the roller 35 in contact with the pipe inner wall, and the camera in the centre of the pipe.

The feed cable 30 is rotatable about its elongate axis (see arrow 36), thereby to change the angular position of the guide wheel within the pipe.

This means the angular position of the wheel can be used to steer the head 32 as it advances in the pipe. By locating the guide wheel within the field of view of the camera (i.e. in front of the camera), the path of the pipe ahead can be visually inspected as well as the current angular orientation of the wheel. Adjustment to the angular orientation can then be made so that the head steers in the desired direction when the feed cable 30 is advanced further.

An ultrasound probe and an ultrasound sensor (together forming an ultrasound head 40) are provided along the feed cable 30. The ultrasound signals are processed and displayed on a display. The resulting ultrasound image provides a representation of the properties of the pipe wall. To do this, the ultrasound signal is scanned around the inner circumference to build up a full image. The ultrasound head 40 is described in more detail with reference to FIG. 3.

FIG. 2 also shows a repair head 60 which enables release of repair materials to a desired location of the pipe. This is described in more detail with reference to FIG. 4.

The different components in FIG. 2 are typically spaced by around 15 cm, and the total length of the cable can be around 100 m. The cable has an outer diameter of approximately 12 mm (typically 10-25 mm).

Figure 3:
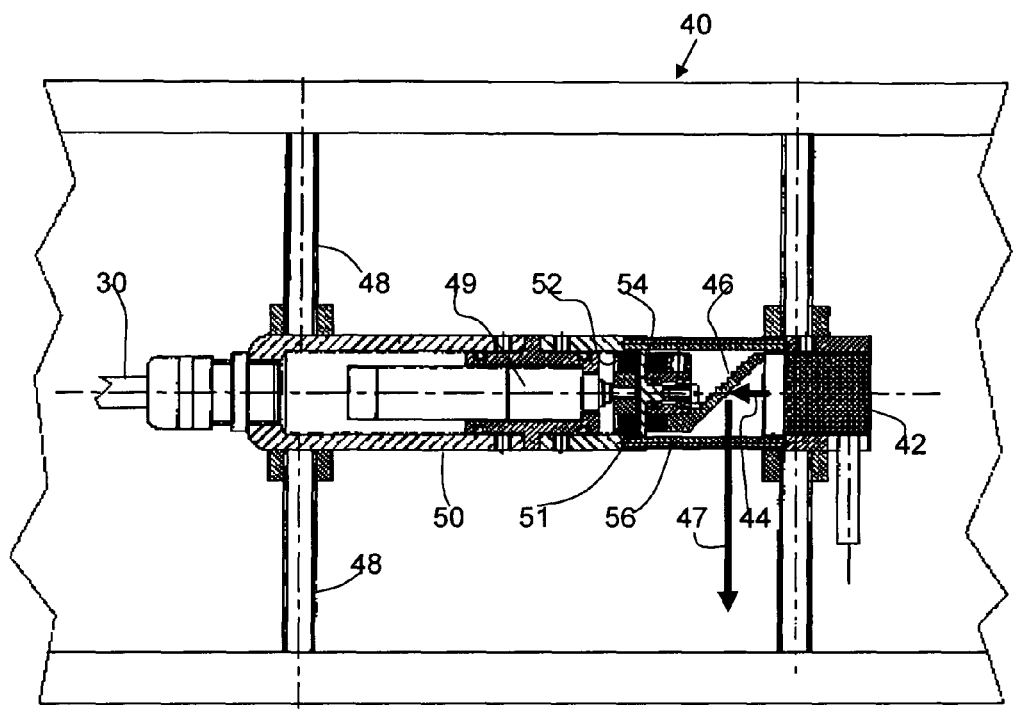
FIG. 3 shows the ultrasound head in more detail.

The ultrasound head 40 shown in more detail in FIG. 3 comprises an output probe 42 which is arranged to direct the probe signal in a direction parallel with the feed cable elongate axis, as shown by arrow 44. A reflector 46 reflects the probe signal to a radial pipe direction 47, and the reflector is rotationally driven to scan all radial directions.

FIG. 3 also shows centring webs 48 which keep the assembly central within the pipe. However, image processing can be used to compensate when the ultrasound head is off-centre.

The rotating reflector is driven by a motor 49 in a sealed (watertight) enclosure 50. The enclosure 50 has an end wall 51, and the motor has an output disc 52 adjacent the end wall 51. The disc has a series of magnets arranged in an annulus of alternating poles. The reflector 46 is driven by an input drive 54 disc adjacent the outer surface of the end wall 51 and which also comprises a magnet arrangement corresponding to the output disc magnets, with opposite poles facing each other.

The two magnet discs together function as a magnetic clutch, which operates across a diaphragm (the end wall) so that one side of the clutch can be in a fluid environment (the reflector) and the other side can be in a sealed gas environment (the motor).

FIG. 3 shows connection tubes 56 which couple the probe 42 to the motor body. The reflector 46 is exposed and open to the liquid in the pipe. The reflected signals are captured by the ultrasound sensor forming part of the unit 42.

The electrical are routed past the reflector in one of the small diameter tubes 56 which hold the probe from the main body. This ensures that electrical noise is present in one position only around the 360 degrees of scanning.

Figure 4:
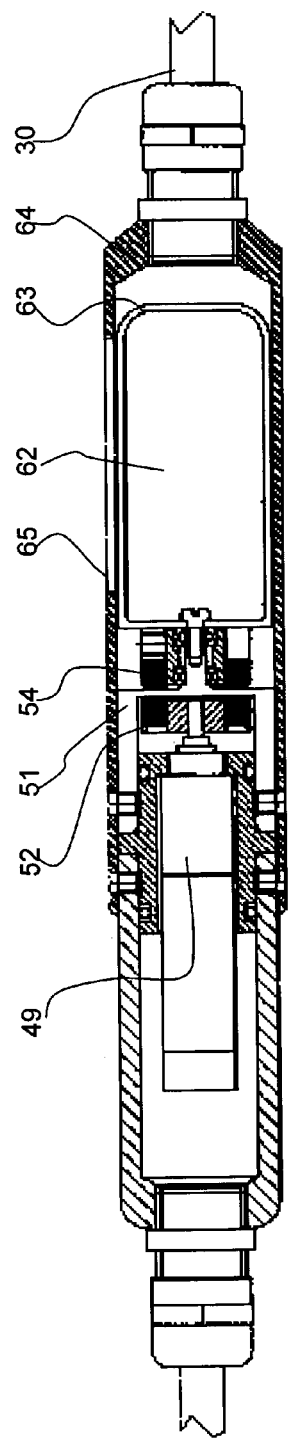
FIG. 4 shows the release chamber in more detail.

FIG. 4 shows the product delivery system 60 in more detail. A product chamber 62 is provided along the feed cable 30 and comprising an inner storage vessel 63 and an outer enclosure 64 having a release aperture 65.

The storage vessel 63 is rotatable relative to the outer enclosure 64 between a first position in which the storage vessel contents are retained, and a second position in which the storage vessel contents can escape through the release aperture. In the escape position, openings in the vessel 63 and the enclosure 64 are aligned.

The vessel is loaded with a treatment material before the system is inserted into the water pipe. This material may for example comprise a silicone consistency material or platelets (for example from the company from Brinker Water—a division of Brinker technology limited), for sealing leaks in the pipe. However, other chemicals or even items of equipment can be stored in the chamber 62 for release into the pipe.

The rotation is controlled by a motor and magnetic clutch system as described with reference to FIG. 3.

The feed cable 30 is driven by a drive arrangement mounted at the launch chamber 22 shown in FIG. 1. This drive arrangement is shown in more detail in FIG. 5.

Figure 5A:
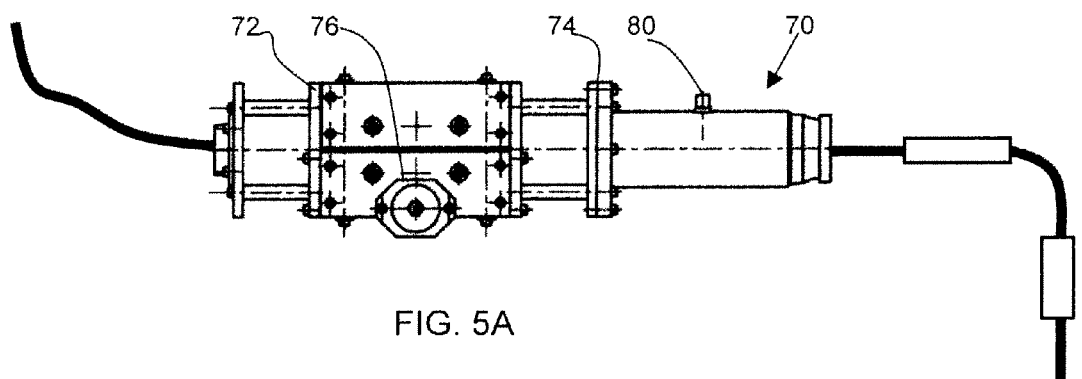
FIG. 5 shows a drive system for driving the system along the pipe.
Figure 5B:
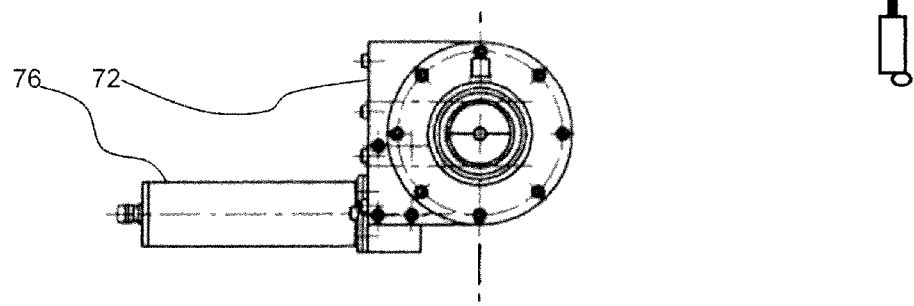

FIG. 5A shows a coupling 70 for connection to the pipe, in particular for connection to the launch chamber 22. This coupling is locked to the hydrant (or other access point) and remains stationary. The main drive part 72 is coupled to the coupling 70 by a bearing arrangement 74 so that it can rotate relative to the coupling 70. The part 72 tightly grips the cable which runs down the centre, and by rotating the unit 72, the angular orientation of the cable can be controlled.

This can be a manual adjustment operation.

The drive part has pairs of roller that are driven by a motor 76 (most clearly shown in FIG. 5B), which can also function as a handle for manual rotation of the cable.

The drive arrangement shown in FIG. 5A is mounted to the hydrant, so that the (right hand) end of the coupling is at the pipe internal pressure. The coupling has a venting arrangement 80 such that the water pipe side of the venting arrangement is at the pressure of the pipe content and the opposite side of the venting arrangement is at a lower pressure. This enables the feed cable to be driven with the pipe at full pressure.

Figure 5C:
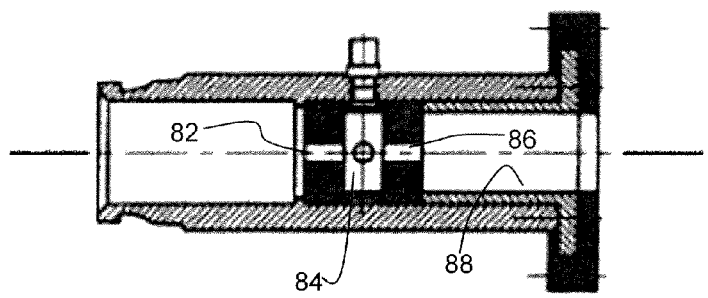

FIG. 5C shows in more detail how the venting arrangement is designed, and shows a cross section through the coupling 70.

The left hand end of the coupling as shown in FIG. 5C is coupled to the hydrant. The venting arrangement 80 comprises a first bore 82 on the pipe side leading to an internal chamber 84. The bore 82 is slightly larger than the feed cable, so that there is small clearance around the feed cable, and the cable is not restricted significantly by friction. For example, the bore may have 12.5 mm diameter, for a 12 mm diameter feed cable. The internal diameter of the coupling 70 can be approximately 5 cm. A second bore 86 is on the opposite, drive mechanism side also leading to the internal chamber 84. The two bores define a passageway through which the feed cable passes, with a small amount of clearance.

The venting arrangement has a bleed screw, so that when the coupling is fitted, the volume expansion between the bore 82 and the chamber 84 provides a pressure drop, and water can be allowed to leak from the bleed screw at a low pressure and flow rate while the inspection/maintenance operation is carried out. Thus, the venting arrangement acts as a pressure void seal, and avoids the need to physical seals to make contact with the feed cable.

The venting arrangement is defined as two halves which fit around the cable. They can be slid in and out of first pipe end of the coupling, and a stop 88 defines their correct installed position. The venting arrangement is fixed in its correct position by the bleed screw.

The drive arrangement is assembled before the apparatus is brought on site. During off-site assembly, the venting arrangement is clamped around the cable after the last piece of equipment. The venting arrangement is then fitted into the coupling 70. The drive arrangement 72 is also clamped around the feed cable. The position of the components in this assembled state, ready for on-site operation, is shown in FIG. 5A.

The drive arrangement defines a volume which can be used to store treatment liquids for treating the cable as it enters the system. For example this can provide an auto chlorinating feature. The drive arrangement shown FIG. 5A simply needs to be mounted vertically (rather than horizontally as shown) and provides a reservoir through which the feed cable is pulled by the drive mechanism. The feed cable is supplied on site on a reel.

The splittable drive arrangement 72 and venting arrangement enables them to be clamped around the cable with the inspection/maintenance components already fitted (whereas these components cannot be fed through the openings of the venting arrangement or drive arrangement). However, in addition, it enables servicing of the drive arrangement and on-site removal of the cable from the coupling 70 (by sliding the venting arrangement out and separating it, so that the coupling can then be slid over the inspection/maintenance components at the remote end of the feed cable).

The feed cable needs to sufficiently rigid to enable pushing into the pipe over long distances, of the order of 100 m. However, the end of the cable needs to be flexible enough to navigate imperfections and bends in the pipe run, and also to facilitate initial insertion of the feed cable into the pipework.

Figure 6:
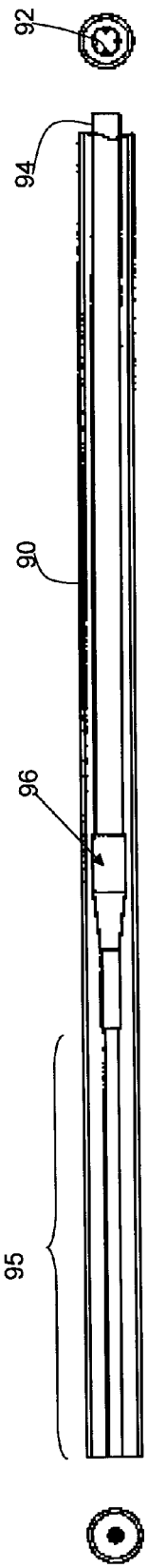
FIG. 6 shows the feed cable in more detail.

FIG. 6 shows a cable design with (at least) two portions with different internal design. An outer casing 90 has constant diameter along the length (designed in combination with the drive arrangement and venting arrangement), for example with 12 mm diameter. Internally, the feed cable comprises reinforcing rods 92 within an outer sheath 94, wherein the outer sheath is narrower in the region 95 of the remote end to provide increased bending flexibility compared to the opposite end of the feed cable. The reinforcing rods can be continuous along the length of the feed cable, and the outer sheath comprises at least one tapered transition section 96. By way of example. the rods can be metal wires, carbon fibre rods or fibreglass strands.

An alternative way to provide the additional flexibility at the end is to use staggered reinforcing rods, so that the number of reinforcing rods diminishes towards the remote end. Flexible dummy rods can be used to keep the cross section constant.

The casing can also house control rods as well as reinforcing rods, and the electrical supply lines are also within the outer casing 90. The electrical cable connections have not been shown in detail. Of course, the motors, lights, camera, sonde, hydrophone and ultrasound head all require electrical power, and signal cables are also needed to route the information back to the operator. These can pass through ducts which are provided as part of the design of each individual component. Wireless signal transmission may of course also be employed.

The system has been described in connection with the inspection or repair of water pipes, and is for gathering information of water main structure and integrity in this example. However, the apparatus can also be used for gas and oil pipes, or other fluid channels.

The example above shows the system inserted at a hydrant. However, the apparatus may equally be inserted at pressure fittings The system has been described with all components in one system. However, each of the components can be used individually, and each has independent advantages and may be suitable for application in different other areas. For the pipe imaging system, the camera head will typically be provided (with or without the steering arrangement and with or without hydrophone). The other components will then optionally be added. Thus typical configurations will be imaging head+ ultrasound, imaging head+release chamber, imaging head+ ultrasound+release chamber.

However, the components can be used in applications, including ones where the camera imaging is not required. Some examples of other uses are:

For the ultrasound imaging, this may be used for pressure vessel imaging, heat exchangers, and indeed any pipework imaging. The reduction in size enabled by the arrangement of the invention also enables parts of the human body to be imaged using the same concepts.

The release chamber can be used in any pressurised fluid pipework i.e. water, petro-chemical.

The drive mechanism can be used for stowing cable or coiling cable. Controlled movement or packing of pulltrusion, rope, wire or rodding. With an encoder on the motor, the arrangement can additionally provide accurate distance measurement.

The magnetic clutch can be used to transmit drive in many applications, for example submersible ROV's or marine drive systems. Fluid pumps could also use this clutch arrangement. Fluid couplings can be replaced with a clutch system as described, and this could avoid the need for cooling or coupling fluids. Any gearbox transmission could be adapted to use the magnetic clutch system.

Various modifications will be apparent to those skilled in the art.

The invention claimed is:

1. A camera inspection system for internal pipe inspection, comprising:
   a feed cable;
   a camera at a remote end of the feed cable, said camera for performing said internal pipe inspection; and
   a guide roller mounted at the remote end of the feed cable having a rotation axis perpendicular to the length of the feed cable, and offset from an elongate axis of the feed cable,
   wherein the feed cable is rotatable about the elongate axis, to change the angular position of the guide roller within the pipe,
   a drive arrangement for driving the feed cable, wherein the drive arrangement comprises:
   a coupling for connection to the pipe, and comprising a venting arrangement such that a first side of the venting arrangement is at the pressure of the pipe content and a second side of the venting arrangement is at a lower pressure; and
   a motor and a roller arrangement within a housing, connected to the coupling, on the second side of the venting arrangement.

2. A system as claimed in claim 1, wherein the guide roller is located within the field of view of the camera.

3. A system as claimed in claim 1, wherein the feed cable comprises reinforcing rods within an outer sheath, wherein the outer sheath is narrower in the region of the remote end to provide increased bending flexibility compared to the opposite end of the feed cable.

4. A system as claimed in claim 3, wherein the reinforcing rods are continuous along the length of the feed cable, and the outer sheath comprises at least one tapered transition section.

5. A system as claimed in claim 1, comprising a probe and a sensor along the feed cable, wherein the probe is arranged to direct a probe signal in a direction parallel with the feed cable elongate axis, and the system further comprises means for redirecting the probe signal to a radial pipe direction, wherein the redirecting means is rotationally driven to scan all radial directions.

6. A system as claimed in claim 1, further comprising:
   a product chamber along the feed cable comprising a storage vessel and a release aperture;
   wherein the storage vessel is controllable between a first configuration in which the storage vessel contents are retained, and a second configuration in which the storage vessel contents can escape through the release aperture.

7. A system as claimed in claim 1, wherein the housing is arranged as at least two sections adapted to be clamped around the feed cable.

8. A system as claimed in claim 1, wherein the housing is rotatable with respect to the coupling thereby to change the angular orientation of the feed cable.

9. A system as claimed in claim 1, wherein the venting arrangement comprises a first bore on the first side leading to an internal chamber, a second bore on the second side also leading to the internal chamber and a vent valve which vents the internal chamber to the outside, and wherein the feed cable passes through the first and second bores, with clearance around the feed cable.

10. A system as claimed in claim 1 comprising an ultrasound probe and a processor for analysing the detected ultrasound signals.

* * * * *